United States Patent
Ries et al.

(10) Patent No.: US 7,988,497 B2
(45) Date of Patent: *Aug. 2, 2011

(54) CONNECTOR ASSEMBLY WITH INTERNAL SEALS AND MANUFACTURING METHOD

(75) Inventors: Andrew J. Ries, Lino Lakes, MN (US); George Patras, Greenfield, MN (US); Thomas J. Olson, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/764,740

(22) Filed: Apr. 21, 2010

(65) Prior Publication Data
US 2010/0204740 A1    Aug. 12, 2010

Related U.S. Application Data

(63) Continuation of application No. 11/608,011, filed on Dec. 7, 2006, now Pat. No. 7,717,754.

(51) Int. Cl.
*H01R 24/04*    (2006.01)
(52) U.S. Cl. ............ 439/669; 439/909; 607/36; 607/116
(58) Field of Classification Search .................. 439/669, 439/668, 736, 909; 607/115, 116, 37, 36
See application file for complete search history.

(56) References Cited

U.S. PATENT DOCUMENTS

| | | | |
|---|---|---|---|
| 3,908,668 A | 9/1975 | Bolduc | |
| 5,534,019 A | 7/1996 | Paspa | |
| 5,669,790 A | 9/1997 | Carson et al. | |
| 5,803,179 A | 9/1998 | Echols et al. | |
| 6,702,624 B2 | 3/2004 | Akimoto et al. | |
| 6,817,905 B2 | 11/2004 | Zart | |
| 6,895,276 B2 * | 5/2005 | Kast et al. | 607/37 |
| 6,980,863 B2 | 12/2005 | van Venrooij et al. | |
| 7,047,077 B2 * | 5/2006 | Hansen et al. | 607/37 |
| 7,083,474 B1 * | 8/2006 | Fleck et al. | 439/668 |
| 7,239,916 B2 | 7/2007 | Thompson et al. | |
| 7,526,339 B2 * | 4/2009 | Lahti et al. | 607/37 |
| 7,717,754 B2 * | 5/2010 | Ries et al. | 439/669 |
| 2003/0163171 A1 | 8/2003 | Kast et al. | |

FOREIGN PATENT DOCUMENTS

WO    WO 2007/101233    9/2007

OTHER PUBLICATIONS

International Search Report, PCT/US2007/086791, Jun. 5, 2008, 5 pages.

* cited by examiner

*Primary Examiner* — T C Patel
*Assistant Examiner* — Travis Chambers
(74) *Attorney, Agent, or Firm* — Carol F. Barry

(57) ABSTRACT

An implantable medical device connector assembly and method of manufacture include a molded, insulative shell having an inner surface forming a connector bore, a circuit member including a one or more traces extending through the shell; one or more conductive members positioned along the connector bore and electrically coupled to the traces; and sealing members positioned between the conductive members.

6 Claims, 8 Drawing Sheets

CONNECTOR ASSEMBLY WITH INTERNAL SEALS AND MANUFACTURING METHOD

CROSS-REFERENCE TO RELATED APPLICATION

The present non-provisional U.S. patent application is a continuation of prior non-provisional patent application having common title and filed on Dec. 7, 2006, and identified by application Ser. No. 11/608,011.

TECHNICAL FIELD

The invention relates generally to implantable medical device connector assemblies and in particular to a device connector assembly including internal seals and an associated method of manufacture.

BACKGROUND

Electrical connectors and other similar electrical components often include electrical conductors embedded within an insulating block to isolate the conductor from the surrounding environment. Embedding the conductor within a block protects the conductor and prevents the delivery of an unintended electrical shock. Electrical connector assemblies are coupled to a hermetically sealed housing of an implantable medical device that encloses internal circuitry such as a hybrid circuit board and one or more batteries. Such a medical device connector assembly is adapted for receiving medical leads used with the implantable medical device.

Methods for forming electrical connector assemblies having conductors embedded within an insulating block may include injection molding techniques or thermoset casting techniques. An improved method for forming an implantable medical device connector assembly with embedded conductors is generally disclosed in U.S. Pat. No. 6,817,905 (Zart et al.), hereby incorporated herein by reference in its entirety. The method generally includes forming a core portion using either an injection molding process or a machining process. The core portion is fitted with electrically conductive components and submitted to a subsequent overmold process in which a second shot of thermoplastic material is injected into the mold. This process allows complex connector structures to be manufactured in a fast production cycle.

In the implantable medical device industry, standards have been developed for lead connector assemblies which are adapted to mate with the device connector assembly. In past practice, lead connector assemblies have included sealing members positioned around insulating structures located between lead connector terminals. The sealing members prevent the ingress of body fluids into a connector bore thereby electrically isolating the connector circuit elements. Ingress of body fluids may otherwise lead to a short circuit between separate connector circuits.

DETAILED DESCRIPTION

In the following description, references are made to illustrative embodiments for carrying out the invention. It is understood that other embodiments may be utilized without departing from the scope of the invention. Unless otherwise indicated, drawing elements are not shown to scale.

Emerging lead connector assemblies, for example assemblies commonly referred to as "IS4" connector assemblies, include in-line lead terminals that are separated by insulating structures but do not include sealing members. A device connector assembly adapted to receive such a connector assembly should therefore incorporate sealing members within the connector bore to provide electrical isolation of the connector circuits. Such sealing members are typically formed as rings fabricated from a supple, biocompatible material, such as silicone rubber. The sealing members are adapted to mate with insulating structures of the connector assembly to form a fluid-resistant seal.

Figure 1:
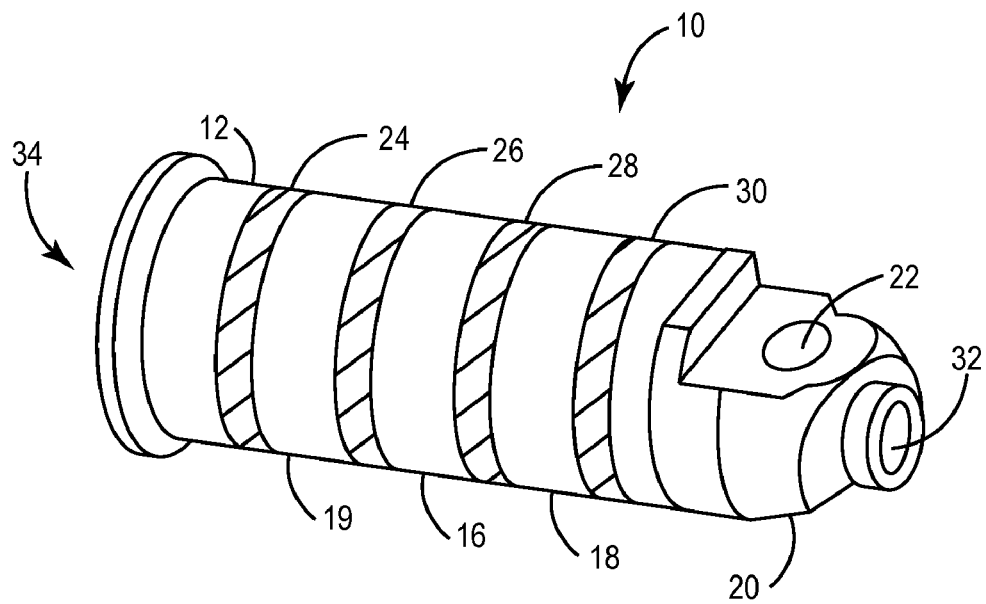
FIG. 1 is a perspective view of a stacked subassembly of conductive members separated by sealing members.

FIG. 1 is a perspective view of a stacked subassembly of conductive members separated by sealing members. Stacked subassembly 10 is used in assembling an implantable medical device connector assembly according to one embodiment of the invention. Stacked subassembly 10 includes an end cap 12 and four conductive connectors 14, 16, 18 and 20 separated by sealing members 24, 26, 28 and 30. Connector 20 is adapted for receiving a lead pin terminal (not shown) and includes an open end aperture 32 through which a pin terminal of a lead connector assembly may be inserted. Connector 20 is shown embodied as a set screw block and further includes a set screw aperture 22 for receiving a set screw (not shown) used for securing the pin terminal of a lead connector assembly to retain the lead connector assembly within a connector bore formed by stacked subassembly 10. Connector 22 may alternatively be embodied as a spring contact or other contact adapted for receiving and engaging a lead pin terminal. The remainder of the connectors 14, 16, and 18 may be embodied as multi-beam contacts, spring contacts, or any other suitable electrical contacts for making electrical connection with lead connector terminals that become aligned with connectors 14, 16, and 18 when the lead connector assembly is fully inserted into stacked subassembly 10. End cap 12 is provided with an open receptacle 34 for receiving a lead connector assembly and acts to terminate the stack. End cap 12 is generally formed of a rigid material which may be conductive or non-conductive.

Sealing members 24, 26, 28 and 30 are fabricated from an insulating material to electrically isolate connectors 14, 16, 18 and 20. Sealing members 24, 26, 28 and 30 are typically formed of a compliant material, such as a medical grade silicone rubber, such that sealing members 24, 26, 28 and 30 form a fluid-resistant seal with insulating structures of a lead connector. When the lead connector is fully inserted into stacked subassembly 10, which has been assembled in an IMD connector assembly, sealing members 24, 26, 28, and 30 will be aligned with insulating structures separating lead connector terminals. An inner surface of sealing members 24, 26, 28 and 30 will form a fluid-resistant interface with the insulating structures of the lead connector assembly, thereby preventing body fluids from creating a short circuit between lead terminals and stacked subassembly connectors 14, 16, 18, and 20.

Figure 2:
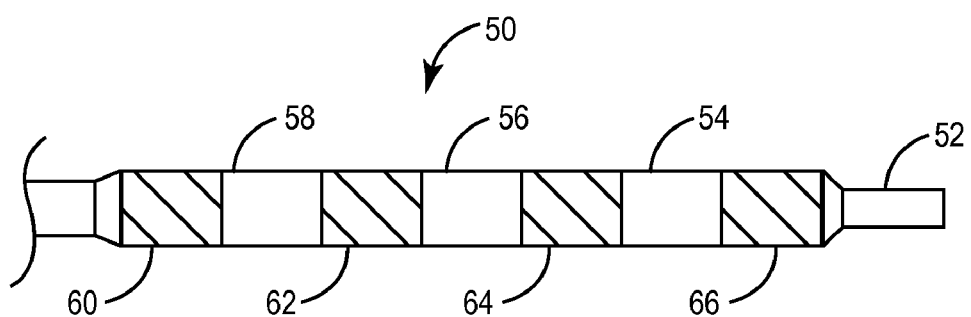
FIG. 2 is a plan view of a proximal lead connector assembly adapted for use with the stacked subassembly of FIG. 1.

FIG. 2 is a plan view of a proximal lead connector assembly adapted for use with the stacked subassembly of FIG. 1. Lead connector assembly 50 includes a pin connector terminal 52 and three ring connector terminals 54, 56, and 58. Lead connector assembly 50 may generally correspond to an IS4 connector assembly, having four inline terminals 52, 54, 56 and 58, however embodiments of the invention may be adapted for use with other lead connector assembly configurations. Each of terminals 52, 54, 56, and 58 are electrically coupled to respective insulated conductors extending through an elongated lead body to electrodes generally positioned along the distal end of the lead body. The terminals 52, 54, 56, and 58 are separated and electrically isolated from one another by insulating structures 60, 62, 64, and 66. Lead connector assembly 50 is commonly referred to as an "in-line" connector assembly in contrast to bifurcated connector assemblies which carry connector terminals on separate branches. In past practice, in-line lead connector assemblies typically have included sealing rings along the insulating structures between connector terminals for providing a fluid resistant seal between circuit elements when the lead connector assembly is coupled to an implanted device. Lead connector assembly 50 does not include such sealing rings. Lead connector assembly 50 is shown having four in-line terminals, though the present invention is not limited to this particular architecture. Embodiments of the invention include device connector assemblies adapted to receive any in-line lead connector assembly, particularly in-line lead connectors that do not incorporate sealing rings on the lead connector.

Figure 3:
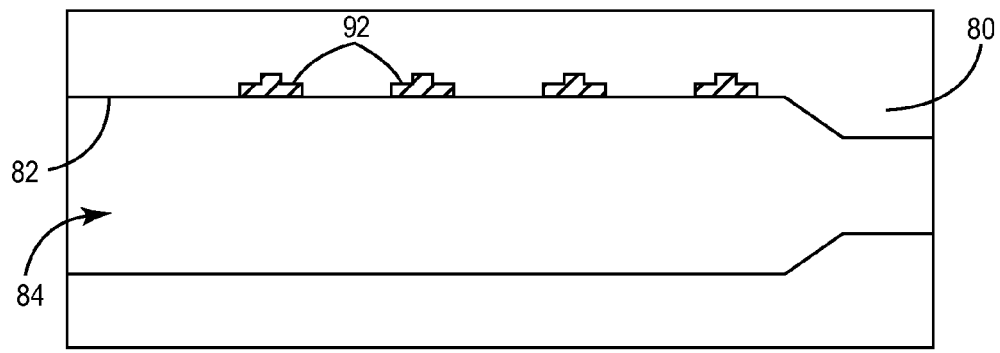
FIG. 3 is a perspective view.
Figure 4:
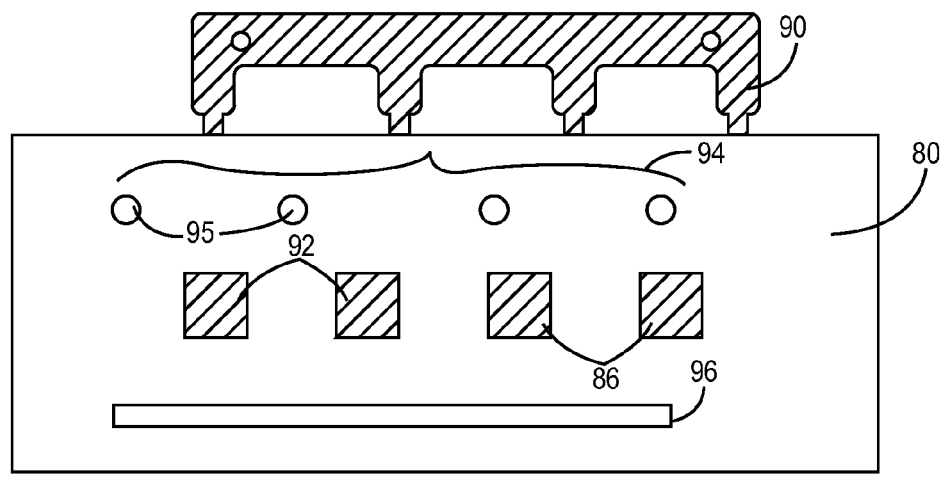
FIG. 4 is a top view of a connector assembly shell according to one embodiment of the invention.

FIG. 3 is a perspective view and FIG. 4 is a top view of a connector assembly shell according to one embodiment of the invention. Shell 80 is formed during a casting or molding process. Shell 80 may be formed from a thermoplastic material, such as a polyurethane, and may thus be formed during high pressure and/or high temperature processes. Suitable polyurethane materials for forming shell 80 include a 75D polyurethane such as Thermedics™ Tecothane® available form Noveon, Inc., Cleveland, Ohio, or Pellethane™ available from Dow Chemical, Midland, Mich. Shell 80 is fabricated by loading a mandrel (not shown) and a circuit member 90 in a mold into which the thermoplastic material is applied. Shell 80 is thereby formed having an inner surface 82, which is formed by the mandrel, defining a connector bore 84. Circuit member 90 is embedded in molded shell 80 such that multiple traces 92 are stably positioned and exposed along connector bore 84. Traces 92 will be subsequently electrically coupled to connectors included in a stacked assembly that will be positioned along connector bore 84. Circuit member 90 is trimmed during manufacturing methods to electrically separate traces 92 and form electrically-isolated conductor paths.

Shell 80 is shown in FIGS. 3 and 4 having a single circuit member represented by circuit member traces 92 and connector bore 84, however it is recognized that a connector shell may be formed having multiple connector bores to allow connection of more than one lead to the associated IMD. Other connector bores may include connector components assembled in the mold which become embedded in shell 80 in an overmolding process, for example as described in the '905 Zart patent.

Shell 80 is formed having multiple windows 86 aligned with circuit member traces 92. Windows 86 provide access for electrically coupling traces 92 to connectors included in the stacked assembly positioned in connector bore 84. Shell 80 further includes a fill port 95, which may include multiple apertures 94 each corresponding to a sealing member location with shell 80. Fill port 95 is used for delivering an adhesive for creating a bond between shell inner surface 82 and sealing members included in a stacked subassembly inserted in connector bore 84. An over fill port 96 is provided to allow excess adhesive and air bubbles to escape during the delivery process.

In alternative embodiments, circuit member 90 may be assembled with shell 80 after molding shell 80. Shell 80 may be formed with channels, grooves, recesses or other features for receiving, retaining and/or aligning conductive traces of circuit member 90. Shell 80 may additionally include other embedded components or be formed with other additional features for receiving components during an assembly process, depending on the particular application.

Figure 5:
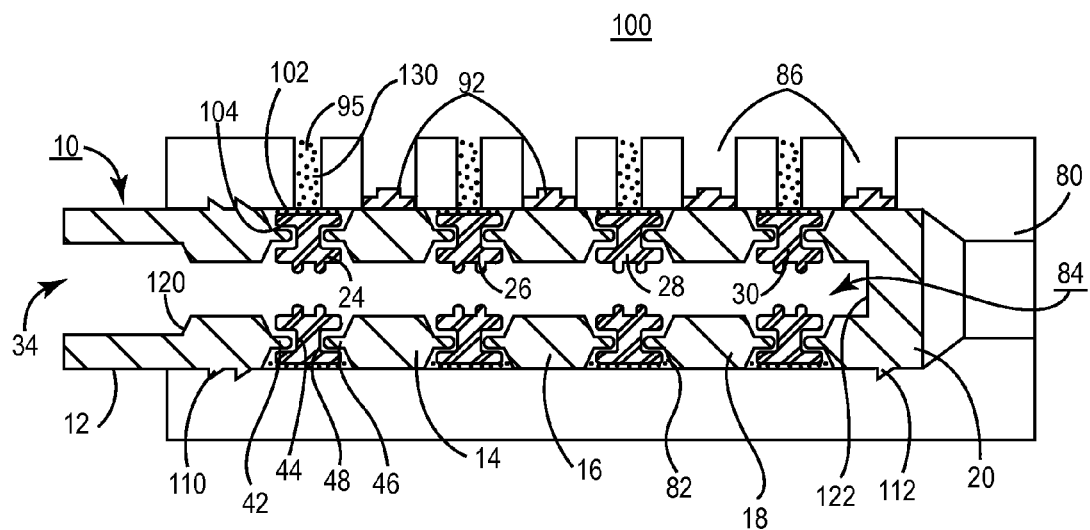
FIG. 5 is a side sectional view of a connector assembly according to one embodiment of the invention.

FIG. 5 is a side sectional view of a connector assembly according to one embodiment of the invention. Connector assembly 100 includes shell 80 that has been molded over circuit member 90 (shown in FIG. 4) to thereby embed portions of circuit member traces 92 within shell 80. Connector bore 84 is formed by shell inner surface 82. The stacked subassembly 10, shown previously in FIG. 1, is fully inserted into connector bore 84 until connectors 14, 16, 18, and 20 are aligned with respective individual traces 92.

During the insertion process, stacked subassembly 10 is loaded onto an insertion tool (not shown in FIG. 5) having a chamfered edge sized to interface with the chamfered inner surface 120 of end cap 12. The tip of the insertion tool is used to apply pressure along inner surface 122 of set screw block 20 and the chamfered edge of the insertion tool exerts pressure along chamfered inner surface 120 until stacked subassembly 10 is fully inserted into connector bore 84. An adhesive, such as an epoxy, a urethane, a silicone medical adhesive, or other suitable thermoset material, is injected through fill port 95 to form adhesive bonds 102 between the outer surface 104 of sealing members 24, 26, 28, and 30 and shell inner surface 82. A two-part adhesive may be premixed prior to injection. Examples of suitable adhesives include epoxy and urethane medical application adhesives available from Master Bond, Inc., Hackensack, N.J. Thus, the stacked subassembly 10 is securely assembled within shell 80 without exposing the compliant sealing members 24, 26, 28 and 30 to the high pressure and/or high temperature process that may be used to form shell 80.

As shown in FIG. 5, stacked components included in subassembly 10 may include interlocking structures for stabilizing the positions of stacked components relative to one another. In the depicted embodiment, end cap 12 is shown having a flange 42 that mates with a groove 44 provided on sealing member 24. Likewise, connector 14 is provided with a flange 46 that mates with a groove 48 on sealing member 24. Such tongue-in-groove structures are shown at each interface between a sealing member and an adjacent component. Other configurations for mechanically interfacing or interlocking adjacent components in stacked subassembly 10 may be used.

End cap 12 may be provided with a retention member 110 for fixedly engaging shell inner surface 82. Connector 20 may additionally be provided with a retention member 112 for fixedly engaging shell inner surface 82. Retention members 110 and 112 are shown as barbs which slide into connector bore 84 formed by inner surface 82 and subsequently engage inner surface 82 to prevent slippage or removal of stacked subassembly 10 from connector bore 84. Other engaging mechanisms may be used to secure stacked subassembly 10 within connector bore 84.

Windows 86 in molded shell 80 allow access for electrically coupling circuit member traces 92 to each of connectors 14, 16, 18 and 20. For example, traces 92 may be laser welded to connectors 14, 16, 18 and 20 through windows 86. Windows 86 are subsequently filled with an insulating adhesive, such as silicone rubber to prevent ingress of body fluids around the circuit member connections. Alternatively, a conductive adhesive may be applied through windows 86 in order to electrically couple traces 92 to connectors 14, 16, 18 and set screw block 20. An insulating adhesive may then be applied over the conductive adhesive to seal windows 86.

In still another embodiment, traces 92 and connectors 14, 16, 18 and 20 are mechanically coupled to provide electrical connection between the traces and the connectors. For example, traces 92 may be pressed, staked, crimpled, or riveted to connectors 14, 16, 18 and 20 through windows 86. Any suitable method for electrically coupling traces 92 to connectors 14, 16, 18, and 20 may be used. Electrical connection of traces 92 with connectors 14, 16, 18 and 20 may occur before or after forming adhesive bonds 102.

Figure 6:
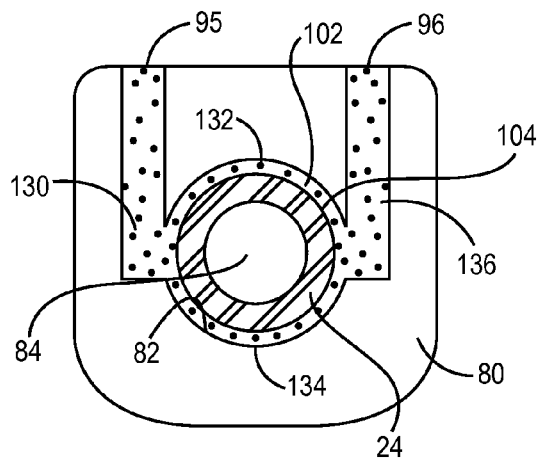
FIG. 6 is an end sectional view of an assembled connector assembly.

FIG. 6 is an end sectional view of an assembled connector assembly 100. Adhesive bond 102 is formed between sealing member outer surface 104 and connector bore inner surface 82 by injecting adhesive through fill port 95. Fill port 95 communicates with channel 130 extending tangentially along connector bore 84. Channel 130 further extends circumferentially around sealing member outer surface 104 forming an upper pathway 132 and a lower pathway 134 along sealing member 24. Channel 130 further extends tangentially forming an exit channel 136 along the opposite side of connector bore 84 extending to over fill port 96. As an adhesive such as epoxy or silicone adhesive is injected into fill port 95, the adhesive will travel along circumferential pathways 132 and 134 to form bond 102. When channels 130 and 136 are completely filled, any excess adhesive and air bubbles will escape through over fill port 96.

Figure 7:
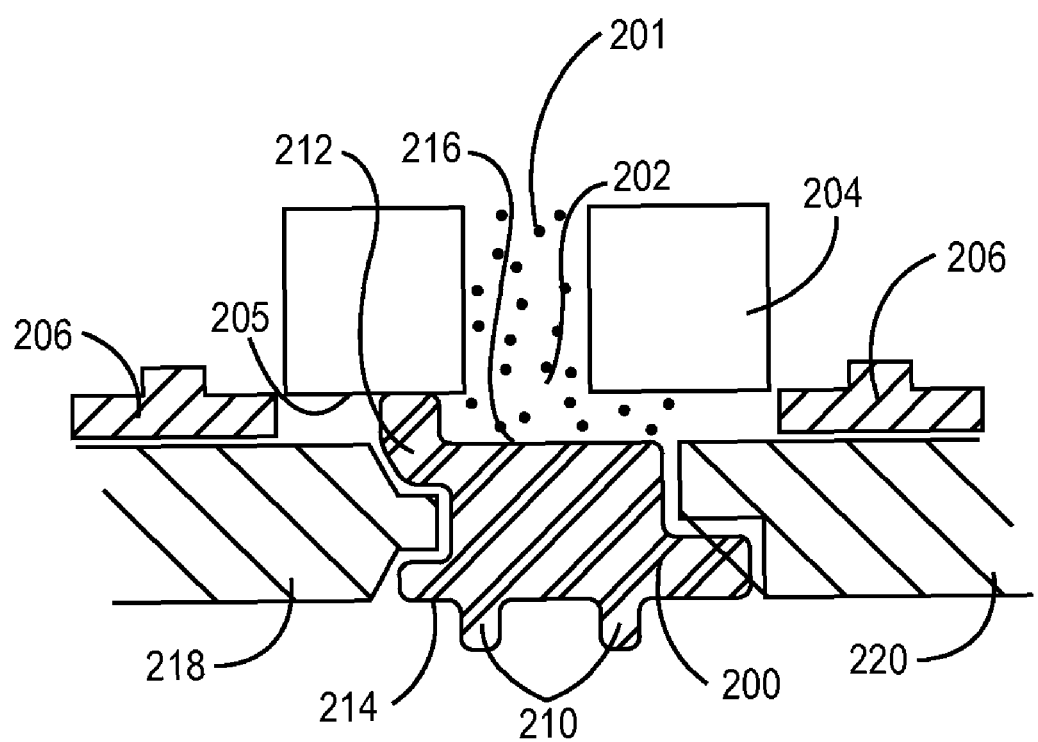
FIG. 7 is a partial sectional view of a connector assembly according to an alternative embodiment.

FIG. 7 is a partial sectional view of a connector assembly 195 according to an alternative embodiment. A connector assembly shell 204 is molded over a circuit member to embed a portion of conductive traces 206 and 208. A stacked subassembly is positioned along a connector bore of shell 204 The stacked subassembly included connectors 218 and 220 electrically coupled to traces 206 and 208, respectively.

Sealing member 200, included in the stacked subassembly and positioned between connectors 218 and 220, includes inner sealing rings 210 extending along inner surface 214 of sealing member 200. Inner sealing rings 210 form a fluid-resistant interface with insulating structures 60, 62, 64, and 66 (shown in FIG. 2) included along a lead connector assembly 50 (shown in FIG. 2) when the lead connector is inserted in the connector bore of shell 204. Sealing member 200 further includes an outer sealing ring 212 extending along outer sealing member surface 216 for interfacing with the inner surface 205 of shell 204. Thus, sealing member 200 forms a fluid-resistant seal with a lead connector insulating structure along inner sealing rings 210 and with shell inner surface 205 along outer sealing ring 212. An optional adhesive bond 202 may be formed between sealing member outer surface 216 and shell inner surface 205 by injecting an adhesive through fill port 201. In some embodiments, adhesive bond 202 is not formed, and fill port 201 is not included in shell 204.

Figure 8:
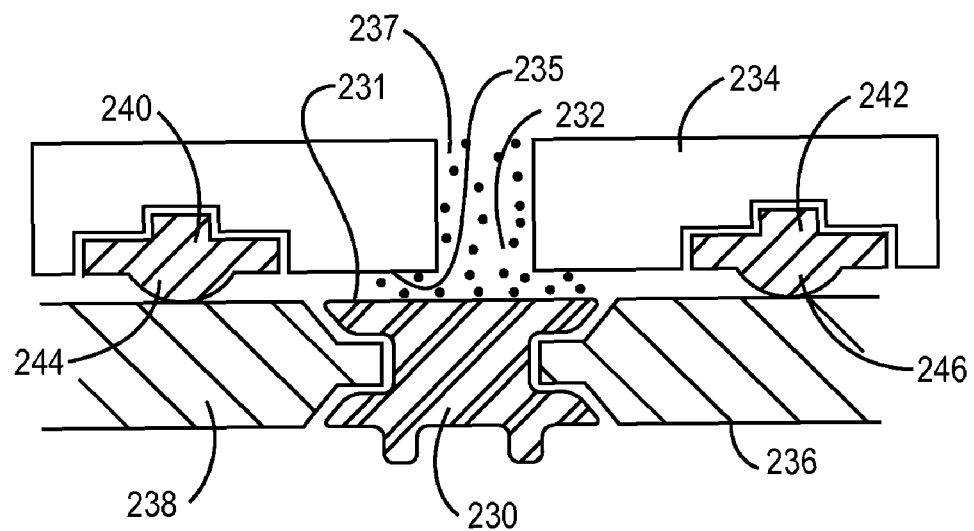
FIG. 8 is a partial sectional view of a connector assembly according to another embodiment of the invention.

FIG. 8 is a partial sectional view of a connector assembly 225 according to another embodiment of the invention. Shell 234 is molded over a circuit member, embedding a portion of conductive traces 240 and 242. A stacked subassembly including connectors 238 and 236 separated by sealing member 230 is inserted in the connector bore of shell 234. Conductive traces 240 and 242 are each provided with a protruding member 244 and 246, respectively, for interfacing with connectors 238 and 236. Protruding members 244 and 246 form a mechanical joint to provide a mechanical and electrical coupling between conductive traces 240 and 242 and connectors 238 and 236, respectively. Shell 234 in this embodiment is formed without windows, as described in previous embodiments, for providing access to perform welding or other forms of electrical coupling of traces 240 and 242 to connectors 238 and 236. Protruding members 244 and 246 may be embodied as a button, barb, spring, beam, or any other mechanical coupling member. Shell 234 is shown to include fill port 237 for injecting an adhesive for forming a bond 232 between shell inner surface 235 and sealing member outer surface 231.

Figure 9:
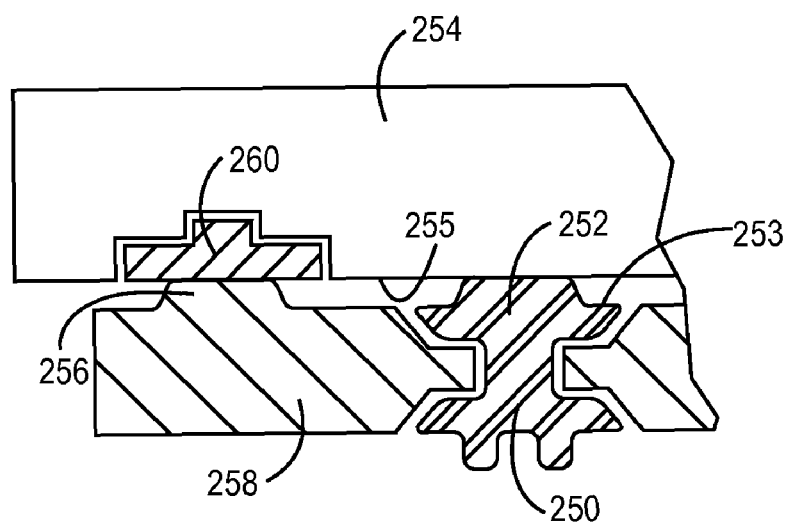
FIG. 9 is a partial sectional view of yet another embodiment of a connector assembly.

FIG. 9 is a partial sectional view of yet another embodiment of a connector assembly. Connector shell 254 is molded over a circuit member, embedding a portion of conductive trace 260. A stacked subassembly including sealing member 250 and connector 258 is inserted in the connector bore of shell 254. Sealing member 250 is provided with an outer sealing ring 252 along the outer surface 253 of sealing member 250. Sealing ring 252 interfaces with the inner surface 255 of shell 254 forming a fluid-resistant seal.

Connector 258 includes a protruding member 256 for interfacing with conductive trace 260. Protruding member 256 provides mechanical and electrical coupling between connector 258 and trace 260. Shell 254 is shown without a fill port or an electrical coupling window. Electrical coupling between conductive trace 260 and connector 258 is achieved by the mechanical coupling of connector 258 and trace 260 created by protruding member 256 upon insertion of the stacked subassembly into the shell connector bore. Likewise, a fluid-resistant interface between shell inner surface 255 and sealing member 250 is formed by sealing ring 252 upon insertion of the stacked assembly within the connector bore of shell 254. Additional electrical coupling and adhesive bonding steps are optional. Accordingly, shell 254 may be provided with or without an injection port and/or electrical coupling windows.

Figure 10A:
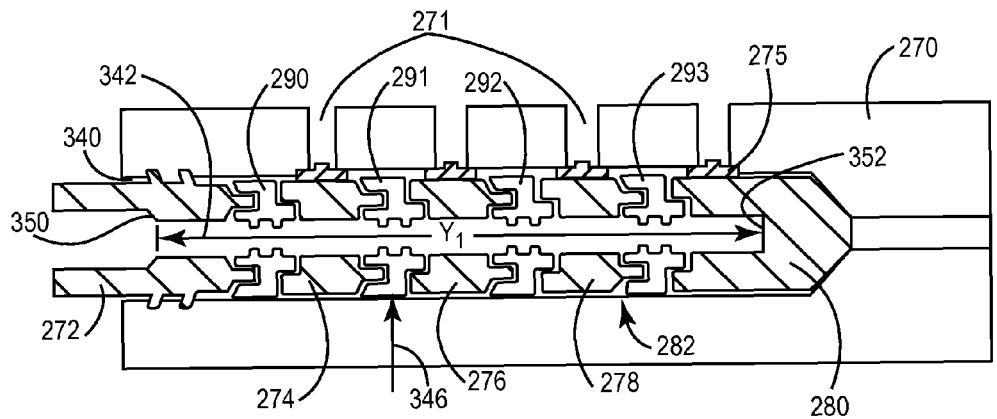
FIG. 10A is a sectional view of a connector assembly according to another embodiment of the invention.

FIG. 10A is a sectional view of a connector assembly according to another embodiment of the invention. In FIG. 10A, a stacked subassembly 282 is inserted in the connector bore 340 of molded shell 270. Stacked subassembly 282 includes end cap 272, connectors 274, 276, 278 and 280, and sealing members 290, 291, 292, and 293. Shell 270 is molded over a circuit member to partially embed multiple conductive traces 275.

Figure 10B:
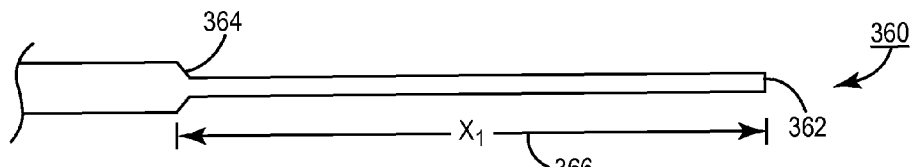
FIG. 10B is a plan view of an insertion tool used to insert a stacked subassembly into a connector bore of a connector shell.

Stacked subassembly 282 is inserted into connector bore 340 using an insertion tool 360 shown in FIG. 10B. Insertion tool 360 includes a tip 362 adapted to engage with the inner surface 352 of connector 280. Tool 360 further includes a chamfered surface 364 adapted to engage with chamfered surface 350 of end cap 272. Insertion tool 360 is characterized by a length $X_1$ 366 between chamfered surface 364 and tip 362. Length $X_1$ 366 corresponds to an uncompressed length $Y_1$ 342 of stacked subassembly 282 extending between inner surface 352 of connector 280 and chamfered edge 350 of end cap 272. Sealing members 290, 291, 292, and 293 are characterized by an outer diameter indicated by arrow 346 when positioned in a substantially uncompressed state as shown in FIG. 10A.

Figure 10C:
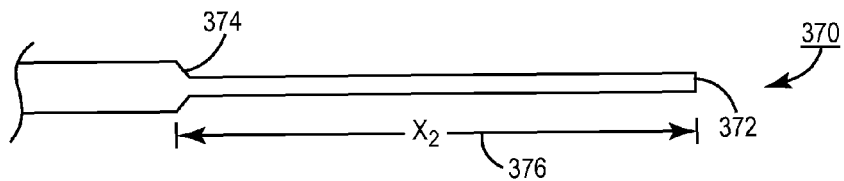
FIG. 10C is a plan view of an insertion tool used to compress a stacked subassembly within a connector bore of a connector shell.
Figure 10D:
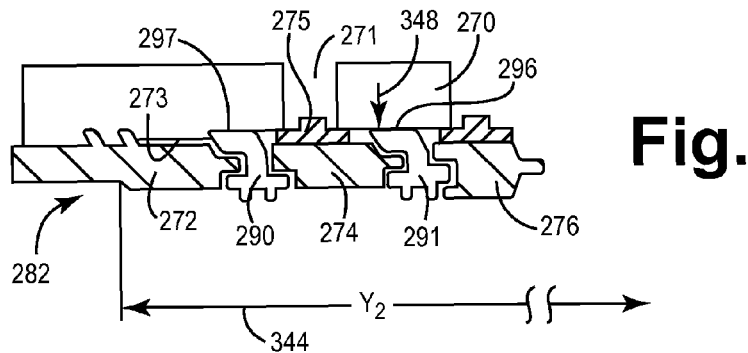
FIG. 10D is partial, sectional view of a compressed stacked subassembly within a connector bore.

Stacked subassembly 282 is fully inserted into connector bore 340 using insertion tool 360 shown in FIG. 10B. Stacked subassembly 282 is then compressed using insertion tool 370 shown in FIG. 10C. Insertion tool 370 is characterized by a length $X_2$ 376 extending between tip 372 and chamfered surface 374. Length $X_2$ 376 is less than length $X_1$ 366 of tool 360. Length $X_2$ 376 corresponds to a compressed length $Y_2$ 344 of stacked subassembly 282 as shown in the partial, sectional view of FIG. 10D. Axial compression of stacked subassembly 282 within connector bore 340 of shell 270 causes radial expansion of sealing members 290 through 293. In a compressed state, sealing members 290, 291, 292, and 293 are characterized by an increased outer diameter as indicated by arrow 348. For example, in one embodiment the sealing members 290 through 293 have an outer diameter of about 0.200 inches in an uncompressed state. Sealing members 290 through 293 expand radially outward upon compression by approximately 5% to 10% deformation resulting in an outer diameter 348 of about 0.210 to 0.220 inches. As shown in FIG. 10D, outward expansion of sealing members 290 and 291 cause the outer surfaces 296 and 297 of sealing members 290 and 291 to interface with the inner surface 273 of shell 270, forming a fluid-resistant seal there between. At the compressed length $Y_2$ 344, the connectors 274 through 280 are properly aligned with conductive traces 275. Electrical coupling of traces 275 with individual connectors 274, 276, 278, and 280 may be performed through windows 271.

Figure 11:
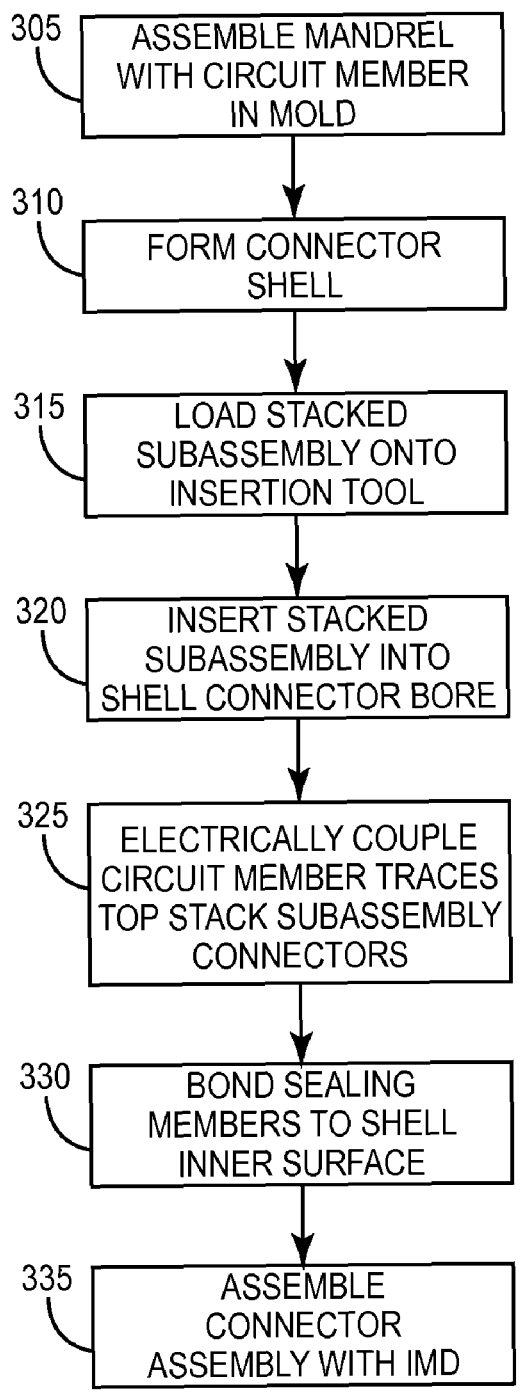
FIG. 11 is a flow chart for an assembly method according to one embodiment of the invention.

FIG. 11 is a flow chart summarizing steps included in an assembly method according to one embodiment of the invention. Method 300 includes assembling a mandrel in a mold for forming a connector shell at block 305. The connector shell is molded at block 310, typically using a thermoplastic material such as polyurethane in a high temperature, high pressure process. A shell inner surface is formed by the mandrel defining a connector bore. The shell may further include other features such as windows for electrically coupling a circuit member to connectors positioned in the connector bore, a fill port for injecting adhesive for bonding the shell inner surface with the outer surface of sealing members positioned in the connector bore, set screw apertures, and other features for accommodating additional connector bores circuit members, connectors, or other components to be included in the connector assembly. As described previously, the circuit member may be assembled in the mold at block 305, prior to injecting the shell material, such that portions of the circuit member are embedded in the molded shell.

At block 315, a stacked subassembly including sealing members, connectors and an end cap, which may be provided with interlocking features, are loaded onto an insertion tool. Using the tool, the stacked subassembly is inserted into the shell connector bore. Retention members may be provided along the stacked subassembly for engaging the shell inner surface and securing the stacked subassembly within the connector bore upon full insertion. A second insertion tool may be used to compress the stacked subassembly within the connector bore.

The individual traces of the circuit member are electrically coupled to the stacked subassembly connectors at block 325. Electrical coupling between circuit member traces and subassembly connectors may be performed through windows included in the connector shell and may involve welding, or application of conductive adhesives. Electrical coupling between traces and connectors may additionally or alternatively include mechanical coupling between the traces and connectors involving riveting, staking, crimping or a protruding mechanical coupling member such as a spring, barb, button, or beam.

At block 330, a fluid-resistant interface is formed between the outer surface of the sealing members and the inner surface of the connector shell. A thermoset material may be injected into fill ports provided in the connector shell to bond the outer surface of the sealing members included in the stacked subassembly to the shell inner surface. After the thermoset adhesive has cured, the connector assembly is assembled with an IMD at bock 335. In alternative embodiments, formation of the fluid-resistant interface may additionally or alternatively include positioning an outer sealing ring extending along the outer surface of the sealing member against the shell inner surface during insertion of the stacked subassembly. In other embodiments, the fluid-resistant interface is formed by compressing the stacked subassembly to cause outward radial expansion of the sealing members.

Figure 12:
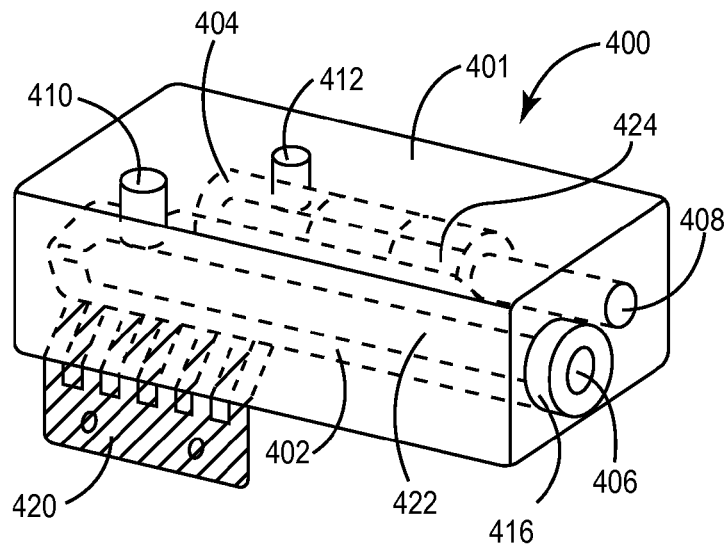
FIG. 12 is a perspective view of a device connector assembly including a molded shell and stacked subassembly inserted into the bore of the molded shell according to one embodiment of the invention.

FIG. 12 is a perspective view of a device connector assembly including a molded shell and stacked subassembly inserted into the bore of the molded shell according to one embodiment of the invention. Connector assembly 400 includes molded shell 401 formed during an overmolding process to partially embed circuit member 420. A stacked subassembly 402 is inserted into connector bore 422, indicated by dash-dot line, having receptacle 406 in end cap 416 for receiving a lead connector assembly. Connector assembly 400 may further include one or more additional receptacles for receiving additional leads in one or more additional connector bores. In the example shown, connector assembly 400 includes a second receptacle 408 for receiving a lead inserted into a second connector bore 424. Shell 401 may encapsulate connectors 404 positioned in the mold during the overmolding process, along the second connector bore 424. In the embodiment shown, circuit member 420 includes traces extending to connectors included in stacked subassembly 402 along connector bore 422 and to the overmolded connectors 404 included along connector bore 424. Thus, connector assembly 400 may include multiple connector bores, which may further include any combination of overmolded connectors and connectors inserted as stacked subassemblies into the connector bore after molding connector shell 401.

Connector assembly 400 includes a set screw aperture 410 for receiving a set screw advanced into a set screw block positioned along connector bore 422. Connector assembly 400 may include additional set screw apertures 412 as needed for receiving additional set screws used for securing lead connector assemblies positioned in other connector bores 424. Connector assemblies may alternatively be fabricated with other connectors in place of set screw blocks, such as spring connectors, for receiving lead connector pins, thereby eliminating the need for set screw apertures.

Figure 13:
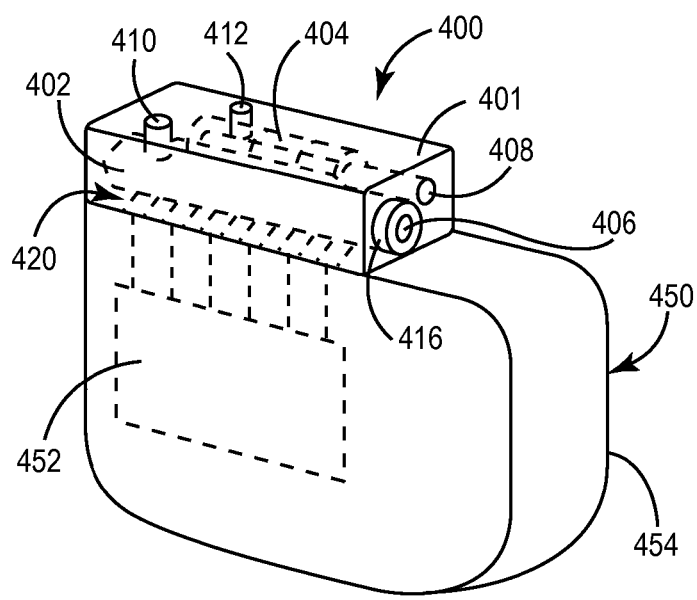
FIG. 13 is a perspective view of the completed connector assembly shown in FIG. 12 coupled to an IMD.

FIG. 13 is a perspective view of the completed connector assembly 400 shown in FIG. 12 coupled to an IMD 450. IMD 450 may be a pacemaker, cardioverter/defibrillator, neurological stimulator, physiological monitor, or any other implantable medical device utilizing medical leads. In particular, sealing members are provided along a stacked subassembly 402 for creating a fluid-resistant seal with insulating portions of a lead connector assembly inserted into receptacle 406. The sealing members also form a fluid-resistant interface with the inner surface of shell 401 along the outer surface of the sealing members. Stacked subassembly 402 is assembled on an insertion tool and assembled in connector shell 401 after shell 401 has been molded. Circuit member 420, partially embedded in connector shell 401, has been trimmed and electrically connected to internal circuitry 452 enclosed in IMD housing 454. Electrical connection between IMD internal circuitry 452 and circuit member 420 is typically made via a feedthrough array extending through hermetically sealed housing 454.

Thus, an electrical medical device connector assembly incorporating sealing members and an associated fabrication method have been presented in the foregoing description with reference to specific embodiments. It is appreciated that various modifications to the referenced embodiments may be made without departing from the scope of the invention as set forth in the following claims.

The invention claimed is:

1. An implantable medical device connector assembly adapted for receiving a medical electrical lead having a lead connector assembly, comprising:
   a molded, insulative shell having an inner surface forming a connector bore,
   a circuit member including a plurality of conductive traces extending through the shell; and
   a stacked subassembly positioned along the connector bore, the stacked subassembly having a bore opening adapted to receive a lead connector assembly, the stacked subassembly comprising:
   a plurality of conductive members positioned along the connector bore and electrically coupled to the plurality of traces, each of the conductive members comprising a flange portion having an upper surface facing toward the shell inner surface; and
   a plurality of sealing members, each sealing member being positioned between conductive members and having a main body portion, an outer surface and a flange portion forming a portion of the outer surface, the flange portion establishing a fluid-resistant interface with the inner surface of the shell, each of the sealing members defining an inner surface establishing a fluid-resistant interface with the lead connector assembly;
   wherein the flange portion of each sealing member overlaps the flange portion of an adjacent conductive member so as to be internally supported from underneath by the upper surface of the conductive member flange portion, and wherein each of the plurality of sealing members further comprise an outer sealing ring protruding radially from the sealing member outer surface along the sealing member flange portion.

2. The connector assembly of claim 1 wherein each of the plurality of sealing members further comprise an inner sealing ring protruding radially from the sealing member inner surface for establishing an interference fit with the lead connector assembly inserted into the bore of the stacked subassembly.

3. An implantable medical device, comprising:
   a housing;
   a circuit member including a plurality of conductive traces;
   a molded, insulative connector shell disposed along the housing and having an inner surface forming a connector bore, the plurality of conductive traces extending through the connector shell,
   a plurality of conductive members positioned along the connector bore and electrically coupled to the plurality of traces, the conductive members defining a bore opening adapted to receive a lead connector assembly;
   a plurality of sealing members each being positioned between adjacent conductive members, each of the plurality of sealing members having an outer surface and a flange forming a portion of the outer surface, the flange defining a fluid-resistant interface with the inner surface of the shell, each of the plurality of sealing members defining an inner surface establishing a fluid-resistant interface with the lead connector assembly inserted within the bore opening, wherein each of the plurality of sealing members further comprise an outer sealing ring protruding radially from the sealing member outer surface along the sealing member flange;
   means for providing support to each sealing member flange from beneath the sealing member inner surface in an area of the sealing member that is opposite the fluid-resistant interface with the inner surface of the shell, and
   internal circuitry enclosed in the housing and electrically coupled to the circuit member.

4. The medical device of claim 3 wherein the sealing member support providing means includes an axially-extending flange on each of the plurality of conductive members, the axially-extending flange having an upper surface; and
   wherein the flange of each of the plurality of sealing members overlaps the upper surface of the axially-extending flange of an adjacent conductive member such that the flange of each of the plurality of sealing members is positioned between the upper surface of the axially-extending flange of the adjacent conductive member and the shell inner surface.

5. The medical device of claim 3 wherein each of the plurality of sealing members further comprise an inner sealing ring protruding radially from the sealing member inner surface for establishing an interference fit with a lead connector assembly inserted into the bore of a stacked subassembly.

6. The medical device of claim 3 wherein the flange portion of each of the plurality of sealing members establishing a fluid-resistant interface with the inner surface of the shell without axial compression of the plurality of sealing members when a stacked subassembly is placed within the connector bore.

* * * * *